United States Patent [19]

Peery et al.

[11] Patent Number: 4,522,622

[45] Date of Patent: Jun. 11, 1985

[54] MULTIPLE FLUID PULSE DISPENSER

[75] Inventors: John R. Peery, Palo Alto; James B. Eckenhoff, Los Altos, both of Calif.

[73] Assignee: ALZA Corporation, Palo Alto, Calif.

[21] Appl. No.: 452,522

[22] Filed: Dec. 23, 1982

[51] Int. Cl.³ .............................................. B65D 35/22
[52] U.S. Cl. .................................. 604/191; 604/185; 604/213; 604/410; 222/94
[58] Field of Search ............... 604/191, 181, 183, 185, 604/204, 212–216, 310, 410, 58, 80; 222/386.5, 92, 94, 145; 206/56

[56] References Cited

U.S. PATENT DOCUMENTS

| 3,128,920 | 4/1964 | Volckening et al. | 604/212 |
| 3,452,757 | 7/1969 | Ames | 604/185 |
| 3,508,878 | 4/1970 | Gunders | 222/94 |
| 3,662,928 | 5/1972 | Pogorski et al. | 604/212 |
| 3,756,243 | 9/1973 | Schulte | 604/185 |
| 4,282,986 | 8/1981 | af Ekenstam et al. | 604/212 |

Primary Examiner—C. Fred Rosenbaum
Assistant Examiner—Michelle N. Lester
Attorney, Agent, or Firm—Steven F. Stone; Edward L. Mandell; Paul Sabatine

[57] ABSTRACT

A multiple fluid pulse dispenser comprising a plurality of interconnected fluid reservoirs defined by mating, oppositely directed concavities at least one of which mating concavity is formed from an invertable, preferrably permanently deformable blister. The reservoirs are in fluid communication with an outlet through which the contents of the reservoirs may be dispensed. A preferred embodiment permits fluid to flow through a reservoir after it has been discharged to allow random activation of the individual reservoirs.

10 Claims, 6 Drawing Figures

MULTIPLE FLUID PULSE DISPENSER

FIELD OF THE INVENTION

This invention relates to dispensers for providing a multiplicity of individual fluid pulses of predetermined size and, more particularly, to manually operated pulse dosage dispensers particularly useful for delivering a series of pulses or doses of a fluid composition for use in medical and chemical applications.

BACKGROUND OF THE INVENTION

The prior art is replete with various types of devices for dispensing either individual doses or multiple doses of fluids or solid pellets. Representative devices are shown for example in U.S. Pat. Nos. 2,403,074, 2,768,623, and 3,154,074, which disclose various manually operated dosage forms for dispensing an individual fluid pulse; Nos. 3,736,933, 3,826,409 and 4,111,304 which disclose devices which can be used to dispense a multiplicity of fluid pulses and Nos. 3,311,229, 3,433,352, 3,737,029, and 3,780,856, all of which disclose various types of blister packages which may be used for dispensing a multiplicity of pharmaceutical dosages usually however in the solid form. U.S. Pat. No. 3,613,680 shows that it is known to include a dosage of a soluble material within a flexible bag such as a disposable syringe and No. 3,443,561 shows that it is known to implant single or multiple dosage form dispensers within the human body.

There currently exists a need for a device which is capable of dispensing multiple pulses of predetermined quantities of a fluid substance. While the applications for such devices range from chemical processing to fertilizing, and feeding fish, a major area of application is in the medical field in which the periodic administration of a precisely determined amount of a biologically active material is required. For example, with respect to insulin therapy for diabetes, one of the most common therapeutic techniques comprises the injection of a predetermined amount of insulin at various times during the day. Thus, for example, according to this invention rather than the conventional multiple hypodermic injections, one insertion could be employed which would thereafter serve to introduce a series of pulse dosages rather than have separate repeated punctures thereafter. Similarly, in a more advanced form of insulin therapy employing a small pump such as is disclosed and claimed U.S. Pat. No. 4,340,048 of Eckenhoff for Self Driven Hypodermic Injector; a continuous basal infusion rate can be provided which is supplemented with manually instigated pulses to more precisely adjust to the changing needs of the patient such as occur after eating, for example. Similarly, in various other forms of therapy, periodic pulse dosages of antibiotics or nutrients are added to IV lines, but normally require a separate insertion of a needle or the introduction of a new mini-bag.

In the administration of pulse doses, it is desirable that manual operation be employed and that there be a positive and irreversible dispensing action such that partial dosages cannot be administered nor can dispensed material be sucked back into the device. In addition, it would be desirable that means for dispensing various dosages in various sequences be available and that the condition of the device in terms of amount dispensed and amount still available can be readily and simply observed visually. While devices of the prior art may be capable of performing one or more of these functions, no device is known which has all of the desirable attributes aforementioned, in addition to being simple and inexpensive to construct and extremely compact in size.

Accordingly, it is an object of this invention to provide a manually operated multipulse fluid dispenser.

It is another object of this invention to provide a multidose dispenser in which the status of use is visually observable.

It is another object of this invention to provide a multidose dispenser in which the size of the dose dispensed can be varied in any sequence.

It is another object of this invention to provide a multidose dispenser in which the manually operated dispensing action is irreversible.

These and other objects of the invention will be readily apparent from the following description with reference to the accompanying drawings wherein.

DESCRIPTION OF THE INVENTION

Figure 1:
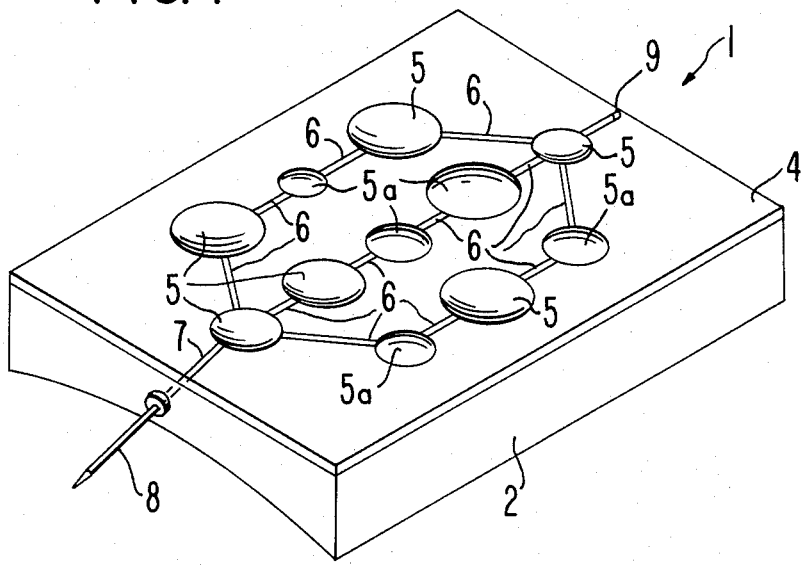
FIG. 1 is a perspective view of one embodiment of this invention.
Figure 2:
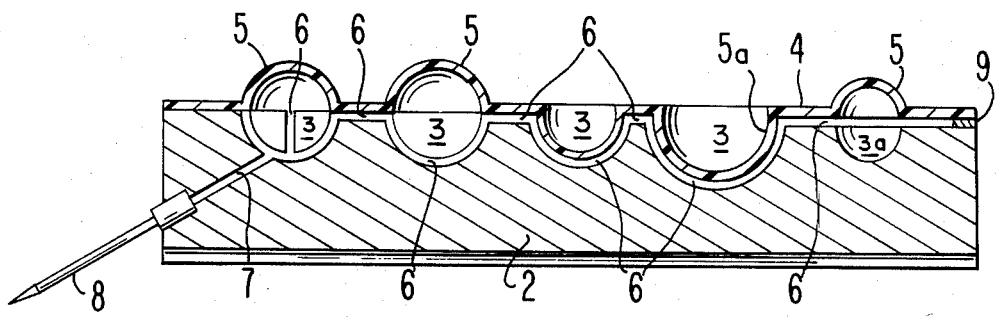
FIG. 2 is a cross-sectional view through the embodiment of FIG. 1.

A manually operated multiple fluid pulse dispenser according to this invention is shown generally as 1 in FIGS. 1 and 2. The dispenser 1 comprises a base member 2 provided with a multiplicity of depressions 3 formed in the base. Overlying base member 3 is a cover sheet 4 provided with a multiplicity of raised blisters 5, which are located above the corresponding depressions 3 to provide therebetween a reservoir for a predetermined fluid volume. The cover 4 and base 2 are bonded to each other substantially across their contacting faces by adhesive or solvent bonding or any other suitable means to provide a fluid tight seal which retains the fluid contents of the reservoir and permits discharge only through passageways 6 specifically provided for that function. Passageways 6 comprise channels in base 2 which, in cooperation with cover 4, provide a fluid flow path between the various reservoirs and a common outlet 7 to which may be attached a needle 8 or any other suitable cannula for conveying the fluid to a distant location. Alternatively, in certain embodiments outlet 7 can merely be left open or provided with a burstable seal for example. The opposite end of the passageway 6 is provided with a puncturable self-sealing septum or plug 9 through which the reservoirs and the passageways can be filled. It is preferable, in order to permit operation of the device in any sequence, to have the channel forming passageway 6 extend both between depressions 3 and along the bottom surface thereof. This will permit fluid to flow through a reservoir to the common outlet after the contents of a reservoir have been discharged by manual pressure on blister 5 to cause it to invert and conform substantially to the shape of the depression 3 as is shown at 5a in FIGS. 1 and 2.

Cover 5 is made from any of a wide variety of materials known to the art for use in blister packaging which are impermeable to the fluid contained within the device and sufficiently flexible to be deformed from their convex initial configuration to the concave final configuration shown at 5a without breaking, while being of sufficient stiffness to resist returning to their original configuration after the pressure of operation is removed. Suitable materials include polyvinyl chloride, polyolefin and polyester resins all as is known to be blister packing art. Typical blister films are approximately 10 mil in thickness.

In the embodiment shown in FIGS. 1 and 2, all of the recesses 3 other than than those shown in the far right of FIG. 1 are provided with grooves in their lower surfaces to permit the flow of fluid after blister 5 is depressed. As is noted above, this is done to permit random access to the contents of the individual reservoirs. Obviously, if a predetermined serial sequence is intended, this feature can be omitted. It should be noted however, that if such a feature is omitted, the possibility of inadvertent, out of sequence, operation still exists. Thus the depression of an intermediate reservoir could have the effect of reversing a previously inverted blister which would then merely fill one of the previously used reservoirs rather than eject a fluid pulse. For this reason it is preferred that passageway means providing flow through used reservoirs be provided even if serial, rather than random, actuation is intended. It is desired to keep the volume of these passageways as small as possible in order to minimize the amount of active material which will remain unused in the device after its blisters have all been actuated. While the grooves in the surfaces of the recesses 3 are a simple and convenient manner of providing for fluid passageways, the invention is not limited thereto and as an alternative, the blister 5 could be sized such that when it is inverted it is not in complete contact with the interior surface 3 leaving a small gap through which fluid flow can occur. Alternatively, the groove can be formed in the interior surface of the blister 5 rather than in the base 2 and and this invention is not limited to the specific means by which the passageways 6 are formed.

As shown in FIGS. 1 and 2, the bottom surface of base 2 is curved slightly so that it may be comfortably attached to the arm or thigh of a patient and secured in place by tape or other suitable fastening means. The needle shown is adapted to be introduced slightly under the skin, however it is readily apparent that the device need not be configured for mounting on the body nor the outlet connected to a needle. Any suitable tubing or other means for delivering the contents to any desired site can be employed. Dispensers may also be connected in series by inserting the needle 8 of one dispenser into the septum 9 of another dispenser for example.

Figure 3:
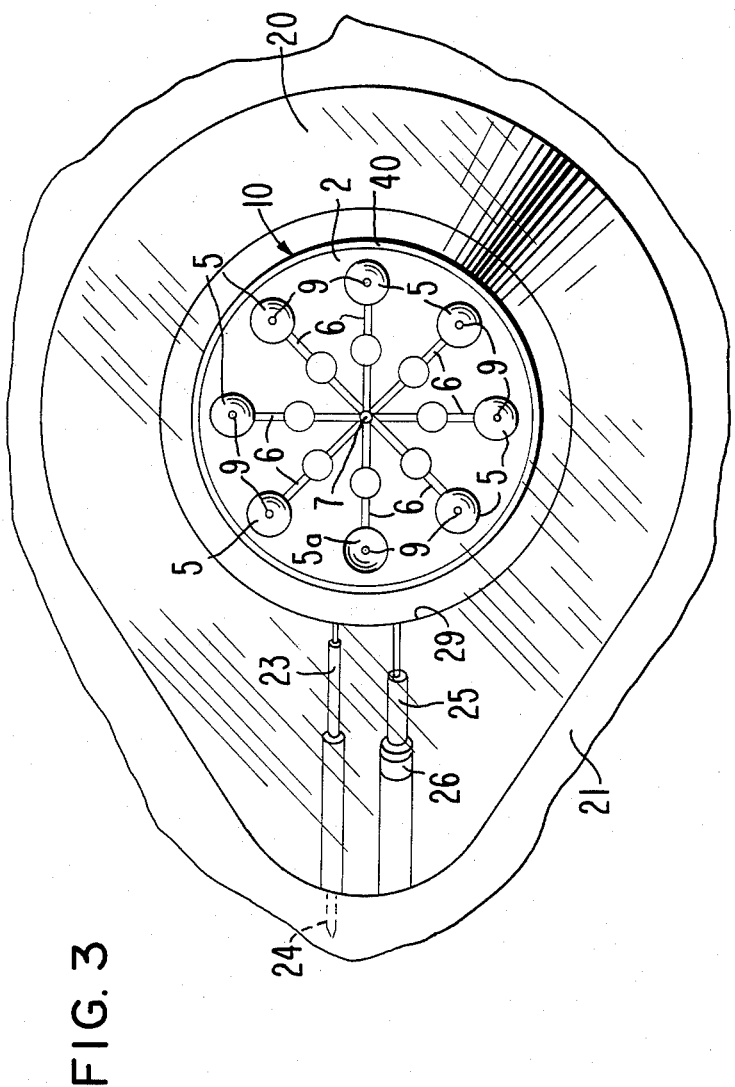
FIG. 3 is a plan view of another embodiment of this invention used in conjunction with a body mounted pump.
Figure 5:
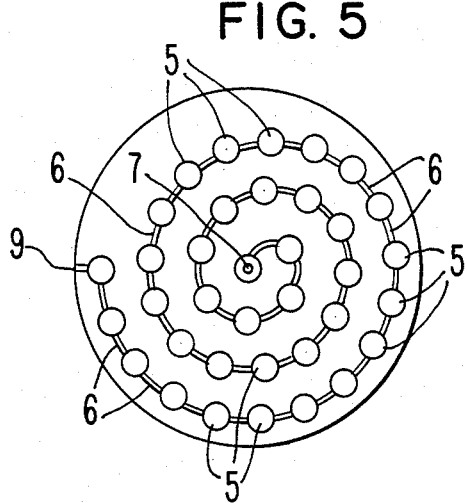
FIG. 5 is a plan view of another embodiment of this invention.

It should be apparent that the shape of the dispenser as well as the pattern of the orientation of the blisters can be varied to adapt the device for any particular contemplated use. Referring now to FIGS. 3 and 5, alternative blister patterns are disclosed. In FIG. 3 the blisters 5 and depressions 3 are arranged in a circular pattern on passageways 6 which extend radially outward, like spokes on a wheel, from a common centrally located outlet 7. In the embodiment of FIG. 5, the blisters 5, depressions 3 and the interconnecting passageway 6 are arranged in a spiral pattern. In FIG. 3, septums 9 are provided for the outermost reservoirs on each spoke to facilitate filling. In FIG. 5, only one septum 9 need be provided.

Figure 4:
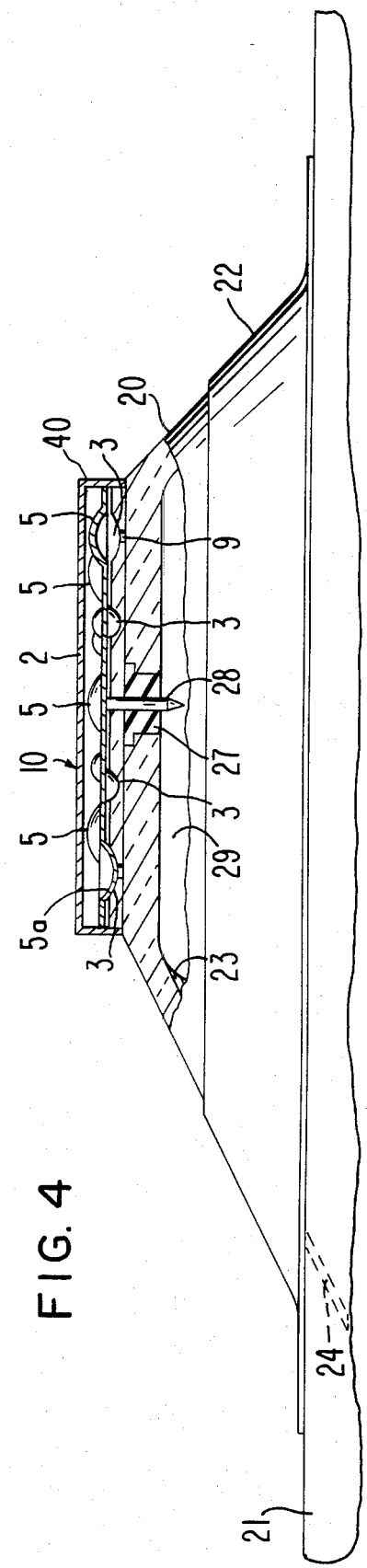
FIG. 4 is a cross-sectional view through the embodiment of FIG. 3.

FIGS. 3 and 4 show a pulse dosage form according to this invention mounted on a infusion pump which is adapted to deliver a constant flow rate of a biologically active fluid to the body of a patient. By combining the pulse dosage form of this invention with such a pump it is possible to provide a dosage regime for those drugs which require a predetermined constant basal flow rate and pulse increases to adjust for changing conditions experienced by the user. Such a regime is common in the treatment of diabetes in which a predetermined basal insulin flow rate is required which is supplemented by additional pulses after meals, for example. The particular structure of the pump with which the multiple pulse dosage form of this invention is used is not part of this invention; however, for illustrative purposes, the pump is shown in conjunction with a pump of the type disclosed and claimed in co-pending, co-assigned patent application of Eckenhoff, et al. for Body Mounted Pump Housing and Pump Assembly Employing the Same, Ser. No. 452,523 filed Dec. 23, 1982. As shown in FIGS. 3 and 4 a pump assembly 20 is mounted on the body 21 of a subject by an adhesive overlay 22 (omitted for clarity in FIG. 3) with the outlet 23 of the pump connected to a hollow needle 24 which is introduced under the skin of the patient. An inlet passageway 25 is blocked with a resealable septum 26 for filling pump. As shown in FIG. 4, outlet 7 of the pulse dosage form 10 is provided with a hollow needle 28 which punctures releasable septum 27 extending through the top wall of pump housing 20. The dosage form 10 is provided with spaced depressions 3 to define between blisters 5 and depressions 3 a multiplicity of reservoirs. Needle 28 is in fluid communication with the displacement chamber 29 of the pump containing the drug to be dispensed such that when one of the blisters 5 is depressed such as 5a a fluid pulse equal in volume to that contained in that reservoir is impressed upon the tonic flow rate and discharged into the subject through needle 24. A protective cap 40 preferably made of a rigid transparent material is provided over the dosage form to prevent inadvertent actuation.

Figure 6:
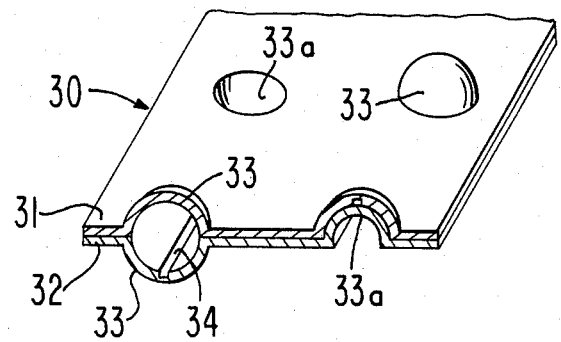
FIG. 6 is a perspective view partially in section of another embodiment of this invention.
Figure 7:
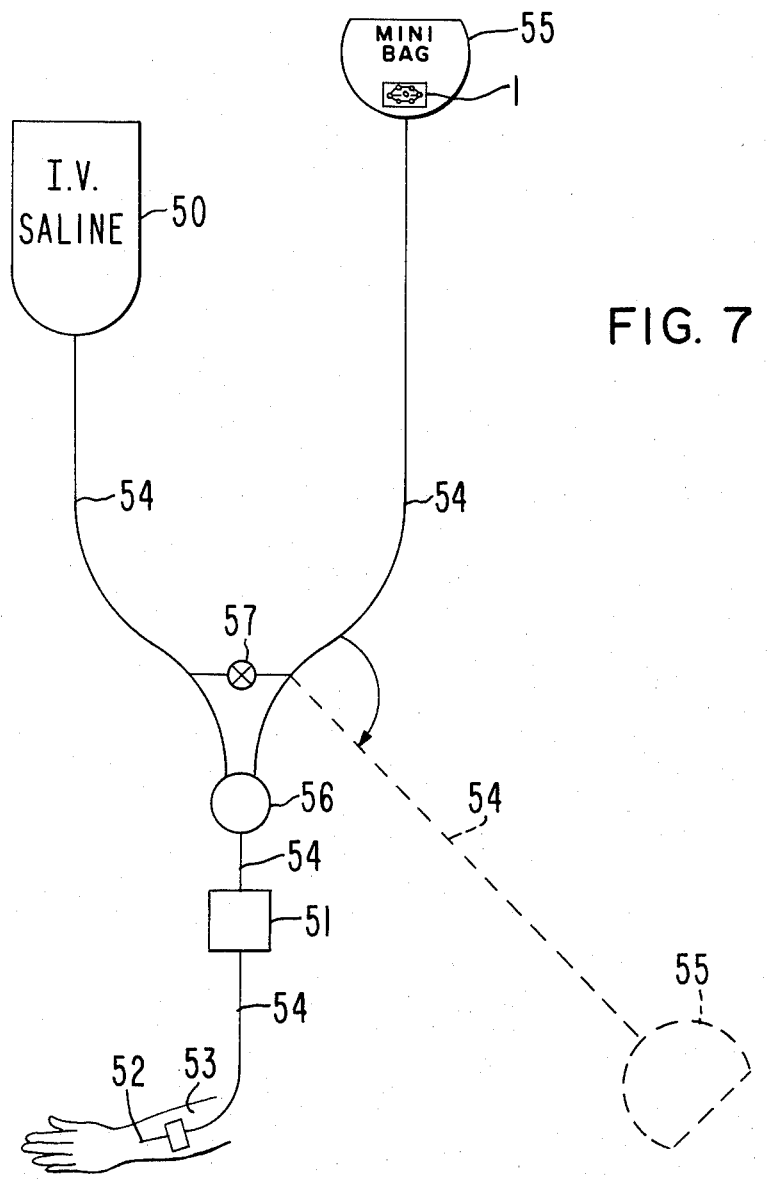

In the embodiments shown in FIGS. 1–5, the base of the device having the depressions in its surface is shown as a relatively rigid structure compared to the deformable cover sheet containing the permanently reversible blisters. It should, however, be readily apparent that the two members between which the volume for each pulse reservoir is defined can be in sheet form. Thus as shown in FIG. 6, dosage form 30 comprises first and second members 31 and 32 formed from the typical sheet material used in blister packaging; each being provided with a multiplicity of opposing blisters 33 which are shown in their used position as 33a. Members 31 and 32 are bonded together by adhesive or fusion or other suitable means at substantially all of their surfaces except at the blisters and in the area of the intercommunicating grooves 34 which are provided in the surface of one or both of the members to permit the operation of the device in random sequence rather than in a predetermined fixed sequence.

As discussed above, the pulse generator of this invention can be used to deliver various substances into an environment of use such as algacides or nutients for an aquarium, fertilizers in a natural or hydroponic gardening, nutrients for growing microorganisms, antiseptics for urinary bags and antibiotics, chemotherapeutic or nutritional agents to IV lines; as some representative non-limiting examples. In those uses, the device would simply be connected to or placed within the environment of use and periodically actuated either directly or through a flexible wall as would be the case with a urinary or I.V. bag.

The pulse dosage forms disclosed herein can either be provided to the pharmacist in empty form and thereafter filled by the pharmacist with any particular drug formulation that is desired simply by insertion of a filling hypodermic needle through the septum and filling the device until a continuous flow of fluid is observed leaving the outlet. Bubbles may be readily removed by tipping the device and visual observation through the transparent cover sheet will verify that bubbles are in fact absent with the device being tipped as necessary to prevent any air from being trapped. Alternatively the devices can be prefilled at a factory and provided to the pharmacist with an appropriate seal over outlet 7.

This invention has been described with respect to specific embodiments thereof and it should not be construed as being limited thereto. Various modifications and substitutions may be made by workers skilled in the art without departing from the scope of this invention which is limited only by the following claims wherein:

We claim:

1. A multiple fluid pulse dispenser for introducing predetermined amounts of a biologically active agent into an animal comprising, in combination:
   (a) a first member having a plurality of spaced apart concavities formed on one surface,
   (b) a second member comprising a plurality of spaced apart permanently invertible blisters, said first and second members being sealed together with the blisters overlaying the concavities so as to provide a plurality of fluid receiving reservoirs, the blister configuration being selected such that, on inversion, the inverted blister will displace substantially all of the fluid contents of its reservoir, and
   (c) fluid communication means connecting said reservoirs to a common outlet means through which the fluid contents of said reservoirs may be dispensed upon inversion of a blister into its associated concavity.

2. The dispenser of claim 1 wherein at least a portion of said reservoirs are connected in series and are provided with fluid flow paths permitting fluid to flow through said reservoir after inversion of its associated blister whereby dispensing of fluid from said reservoirs may occur in a random manner.

3. The dispenser of claim 2 wherein the concavities on said first member comprise a plurality of permanently deformable invertable blisters whereby said dispenser may be actuated from either side.

4. The dispenser of claims 1 or 2 wherein at least a portion of the reservoirs are of different volumes.

5. The dispenser of claims 1, 2 or 3 wherein said outlet is in fluid communication with a hollow needle through which the fluid contents may be dispensed into the body of a recipient.

6. The dispenser of claim 5 further comprising removable cover means overlaying the blisters to prevent unintended depression of said blisters.

7. The dispenser of claim 5 further comprising a biologically active fluid within said reservoirs.

8. The dispenser of claim 5 wherein at least a portion of the reservoirs are of different volumes.

9. The dispenser of claim 2 wherein the reservoir most distal from said outlet means is provided with an inlet port and said inlet port is provided with puncturable resealable sealing means.

10. The dispenser of claim 5 wherein the reservoir most distal from said outlet means is provided with an inlet port and said inlet port is provided with puncturable resealable sealing means.

* * * * *